(12) United States Patent
Boogers et al.

(10) Patent No.: US 6,231,821 B1
(45) Date of Patent: May 15, 2001

(54) PROCESS TO SEPARATE RHODIUM FROM AN ORGANIC MIXTURE

(75) Inventors: Jeroen A. F. Boogers, Maastricht; Theodorus M. Smeets, Stein, both of (NL)

(73) Assignees: DSM N.V., Heerlen (NL); E.I. Du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/584,723

(22) Filed: Jun. 1, 2000

Related U.S. Application Data

(63) Continuation of application No. PCT/NL98/00676, filed on Nov. 30, 1998.
(60) Provisional application No. 60/070,186, filed on Dec. 30, 1997.

(30) Foreign Application Priority Data

Dec. 1, 1997 (EP) .................................................. 97203754

(51) Int. Cl.$^7$ ...................................................... C22B 11/00
(52) U.S. Cl. ................................................................ 423/22
(58) Field of Search .................................. 423/22; 502/25, 502/28, 32

(56) References Cited

U.S. PATENT DOCUMENTS

| 5,145,995 | | 9/1992 | Burke . | |
|---|---|---|---|---|
| 5,364,822 | * | 11/1994 | Carey | ....................... 423/22 |
| 5,908,803 | * | 6/1999 | Leconte et al. . | |

FOREIGN PATENT DOCUMENTS

WO9705949    2/1997   (WO) .

* cited by examiner

Primary Examiner—Steven Bos
(74) Attorney, Agent, or Firm—Pillsbury Winthrop, LLP

(57) ABSTRACT

Process to separate rhodium from an organic starting mixture comprising of an organic solvent, $C_6$-dicarboxylic acids and iodide compounds, wherein rhodium is separated by extracting the organic starting mixture with an aqueous solvent containing $C_6$-dicarboxylic acids and an iodide compound resulting in an organic raffinate poor in rhodium and an aqueous extract rich in rhodium.

10 Claims, 2 Drawing Sheets

PROCESS TO SEPARATE RHODIUM FROM AN ORGANIC MIXTURE

Figure 1:
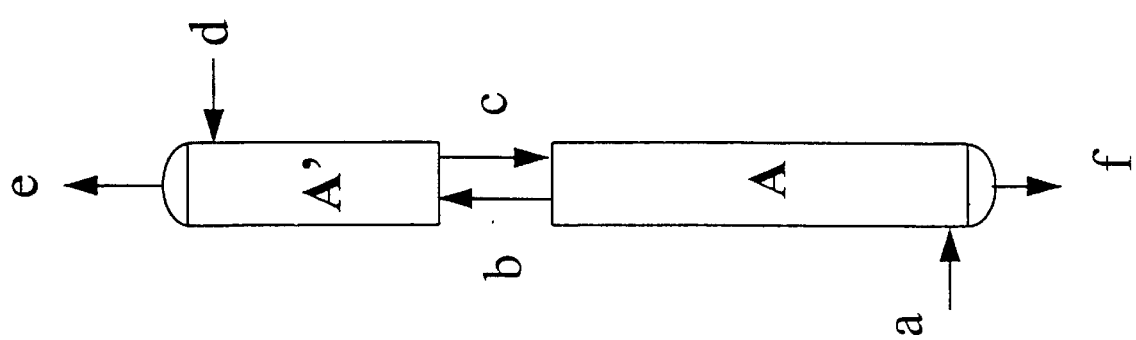

This is a Continuation of, International Appln. No. PCT/NL98/00676 filed Nov. 30, 1998.

This application claims the benefit of U.S. Provisional Application No. 60/070,186, filed Dec. 30, 1997.

The invention relates to a process to separate rhodium from an organic starting mixture comprising an organic solvent, $C_6$-dicarboxylic acids and iodide compounds.

Mixtures comprising rhodium, $C_6$-dicarboxylic acids and iodide compounds are for example obtained as purge streams in the preparation of pentenoic acid as described in EP-A-405433. This patent publication describes the carbonylation of butadiene with water in the presence of carbon monoxide and a catalyst system comprising of rhodium and an iodide promotor compound.

It has been found to be a problem to remove the valuable rhodium from the purge stream. No methods which can be used on a commercial scale have been described for this particular problem. A practical method for removing the rhodium from the purge stream is highly desirable when one wants to operate a commercial plant based on the process according to EP-A-405433. The rhodium obtained from the purge stream is advantageously reused in the carbonylation reactor.

The object of this invention is to obtain a practicable method for removing rhodium from a starting mixture as described above.

This object is achieved in that rhodium is separated by extracting the organic starting mixture with an aqueous solvent containing $C_6$-dicarboxylic acids and an iodide compound resulting in an organic raffinate poor in rhodium and an aqueous extract rich in rhodium.

It has been found that rhodium can be successfully removed from the organic mixture indicated above by extraction. The extraction can be simply operated in a continuous mode on a large scale. When performing a process according to EP-A-405433 it has been found that the resulting aqueous extract containing the rhodium can advantageously be directly returned to the carbonylation reactor.

Without wanting to limit the invention by the following theory it has been found that the extraction efficiency of rhodium from the organic phase to the aqueous phase is highly influenced by the content of the $C_6$-dicarboxylic acids in the two immiscible phases. If the content of $C_6$-dicarboxylic acids in the aqueous phase is near zero the extraction coefficient of rhodium (expressed in $K_{Rh}$=Rh $(ppm)_{water}$/Rh$(ppm)_{organic}$) over the two phases is also low. In contrast a high and preferred $K_{Rh}$ is found to exist when the content of $C_6$-dicarboxylic acids in the aqueous phase is above a certain level. When performing the extraction it is therefore important to maintain a certain level of dicarboxylic acids in the aqueous phase at all times in order to keep rhodium in the aqueous phase. The content of $C_6$-dicarboxylic acids in the aqueous phase can be increased provided that a phase separation will occur. Preferably the $C_6$-dicarboxylic acids in the aqueous phase are in equilibrium with the $C_6$-dicarboxylic acids in the organic phase. This results in that during the extraction (almost) no net exchange of dicarboxylic acids between the two phases will take place.

The ratio of $C_6$-dicarboxylic acids concentration in the aqueous solvent to the $C_6$-dicarboxylic acids concentration in the organic starting mixture is preferably between 1:1 and 5:1. Preferably this ratio is lower than 3:1. Most preferably this ratio is equal to the two-phase equilibrium ratio of the dicarboxylic acids. The equilibrium ratio will depend for example on the composition of the organic starting mixture, temperature and pressure. The $C_6$-dicarboxylic acid in the organic starting mixture is preferably between 10–60 wt. % and in the aqueous solvent between 30–70 wt. %. The $C_6$-dicarboxylic acids are adipic acid, 2-methyl glutaric acid, ethyl succinic acid, dimethyl succinic acid or mixtures thereof.

The organic solvent should be substantially immiscible with water, $C_6$-dicarboxylic acids should dissolve in the solvent and it should be inert during a carbonylation reaction. Preferably the organic solvent is a $C_5$–$C_{13}$ mono-carboxylic acid or mixtures thereof. More preferably $C_8$–$C_{13}$ mono-carboxylic acids or mixtures of these acids are used. $C_9$-carboxylic acids will generally be present when the organic starting mixture is derived from a carbonylation process to prepare pentenoic acid, because $C_9$-carboxylic acids are by-products of this reaction. The $C_9$-carboxylic acids are for example nonanoic acid, nonenoic acid, and branched or cyclic $C_9$-carboxylic acids, or mixtures thereof.

Preferably the aqueous solvent also contains the corresponding $C_5$–$C_{13}$ mono-carboxylic acids. The content of these mono-carboxylic acids in the aqueous phase can be increased provided that a phase separation will occur. The ratio of mono-carboxylic acids concentration in the aqueous solvent to the mono-carboxylic acids concentration in the organic starting mixture is preferably between 1:5 and 1:20. Most preferably this ratio is equal to the two-phase equilibrium ratio of the mon-carboxylic acids. The equilibrium ratio will depend for example on the composition of the organic starting mixture, temperature and pressure. The mono-carboxylic acid concentration in the organic starting mixture is preferably between 40–90 wt. % and in the aqueous solvent between 5–20 wt. %.

The $C_6$-dicarboxylic acids and the $C_5$–$C_{13}$ mono-carboxylic acids (if present) may be added prior to the extraction to pure water to obtain the aqueous solvent to be used in the extraction. The desired composition of the aqueous solvent can also be obtained by performing the exctraction with only water (d): By adding a number of exchange stages in a counter current extraction column (A') relative to the situation in which a aqueous/$C_6$-dicarboxylic acid mixture is directly used (A), it has been found that the desired aqueous composition according to the invention will be obtained at an intermediate position (c) in the extraction column. If the rhodium content is sufficiently low at that position (b) in the column the content of rhodium in the organic raffinate (e) will also be low. The letters A, A' and (a)–(f) refer to FIG. 1. In this Figure stream (f) is the aqueous extract.

If rhodium is to be removed from a purge stream of a carbonylation process as for example described in EP-A-405433 it can be necessary to adjust the composition of the organic mixture before performing the extraction according to the invention. The adjustment of the composition is needed in order to achieve the preferred concentration and ratio's of the mono- and/or di-acids concentration over the phases as described above. A purge stream will generally contain between 10–10000 ppm rhodium, between 10–90 wt % $C_6$-dicarboxylic acids, between 10–90 wt. % $C_5$–$C_{13}$ mono-carboxylic acids and between 10 and 10000 ppm iodide promotor compounds. The purge stream may also contain other high boiling by-products, for example tars, of the carbonylation reaction. In a continuous process also some water may be present in the organic starting mixture because some water will be present in the $C_5$–$C_{13}$ mono-carboxylic acids stream used to mix with the purge stream before extraction.

The aqueous extract will contain some $C_6$-dicarboxylic acids and mono-carboxylic acids (if present), due to their solubility in the water phase. The organic rafinate will, apart from the $C_6$-dicarboxylic acids and mono-carboxylic acids, also contain water due to its solubility in the organic phase. This water is preferably removed from the organic raffinate together with part of the $C_6$-dicarboxylic acids and mono-carboxylic acids. This separation is preferably performed by distillation. Preferably three product streams are obtained in the distillation, namely a water stream, a mono-carboxylic acid stream and a $C_6$-dicarboxylic acid stream. The purity of these product streams is not critical, therefore making a distillation in one column possible. The water stream and part of the $C_6$ and optionally the mono-carboxylic-products are preferably reused in the extraction. The remaining $C_6$-dicarboxylic acids and mono-carboxylic acids can be disposed of.

The amount of $C_6$-dicarboxylic acids and mono-carboxylic acids in the aqueous extract will be lower than the amount present in the original purge stream.

The extraction is generally performed at a temperature betweem 0–100° C. and preferably between 30–60° C. The lower temperature limit is not critical, provided that the temperature is sufficiently high in order to keep the compounds in the fluid state. The pressure is not critical, provided that phase separation will take place. The pressure may be between 0.1 and 1 MPa. Preferably the extraction is performed in the presence of carbon monoxide. Preferably the CO-partial pressure is higher than 5 mmbar. The presence of carbon monoxide prevents rhodium precipitation.

The process according the invention is especially advantageous for removing rhodium from a purge stream in a process to prepare pentenoic acid from butadiene (or a butadiene derivative) or adipic acid from pentenoic acid in which use is made of a rhodium/iodide promoter catalyst system. Exemplary processes are disclosed in EP-A-405433, EP-A-428979 and EP-A-188209.

The iodide compound in the organic starting mixture may be any of the promoters cited in these references. Preferably the iodide compound is HI or butyl iodide. Most preferably HI is used. When HI is used the mixture can also contain iodide compounds formed by reaction of HI and the compounds present during the carbonylation, for example crotyl iodide and butyl iodide. The molar ratio of the iodide compound and rhodium in a purge stream obtained in such a carbonylation process is generally higher than 1:1 and mostly higher than 2:1. The upper limit is not critical and will be limited by the solubility of the iodide compound in water.

It has been found that some iodide present in the aqueous solvent is essential to achieve a good extraction efficiency of rhodium. The content iodide compound in the aqueous solvent is preferably between 0.01 and 10 wt % and more preferably between 0.5 and 5 wt. %. Because of the high affinity of inorganic iodide compounds, for example HI, for water most of these iodide compounds will be present in the resulting aqueous extract.

The extraction process according to the invention is preferably performed continuously. The contacting can be performed the usual liquid-liquid contactors, for example a series of mixer-settlers, pulsed packet columns or rotating disc columns. The process is preferably performed in a counter currently operated vertically placed vessel, wherein to the top of the vessel the aqueous solvent is fed and to the bottom the organic starting mixture is fed. The aqueous extract and the organic raffinate are obtained at the bottom and top of the column respectively. The column has preferably 5 or more theoretically exchange stages.

The invention is especially directed to a process to continuously prepare pentenoic acid by carbonylation of butadiene or a butadiene derivative and water in the presence of a catalyst system comprising rhodium and a HI promoter compound and a $C_8$–$C_{13}$ mono-carboxylic acid solvent in which the following steps are performed, (a) separation of the pentenoic acid product from the carbonylation reactor effluent resulting in a mixture containing the catalyst system and $C_6$-dicarboxylic acids and mono-carboxylic acids, (b) returning said catalyst containing mixture to the carbonylation reaction, (c) purging part of said catalyst containing mixture and removing rhodium from the purge stream according to the process according the invention as described above, (d) returning the aqueous extract obtained in step (c) to the carbonylation reaction.

The carbonylation can be performed according to the conditions as described in EP-A-405433.

Figure 2:
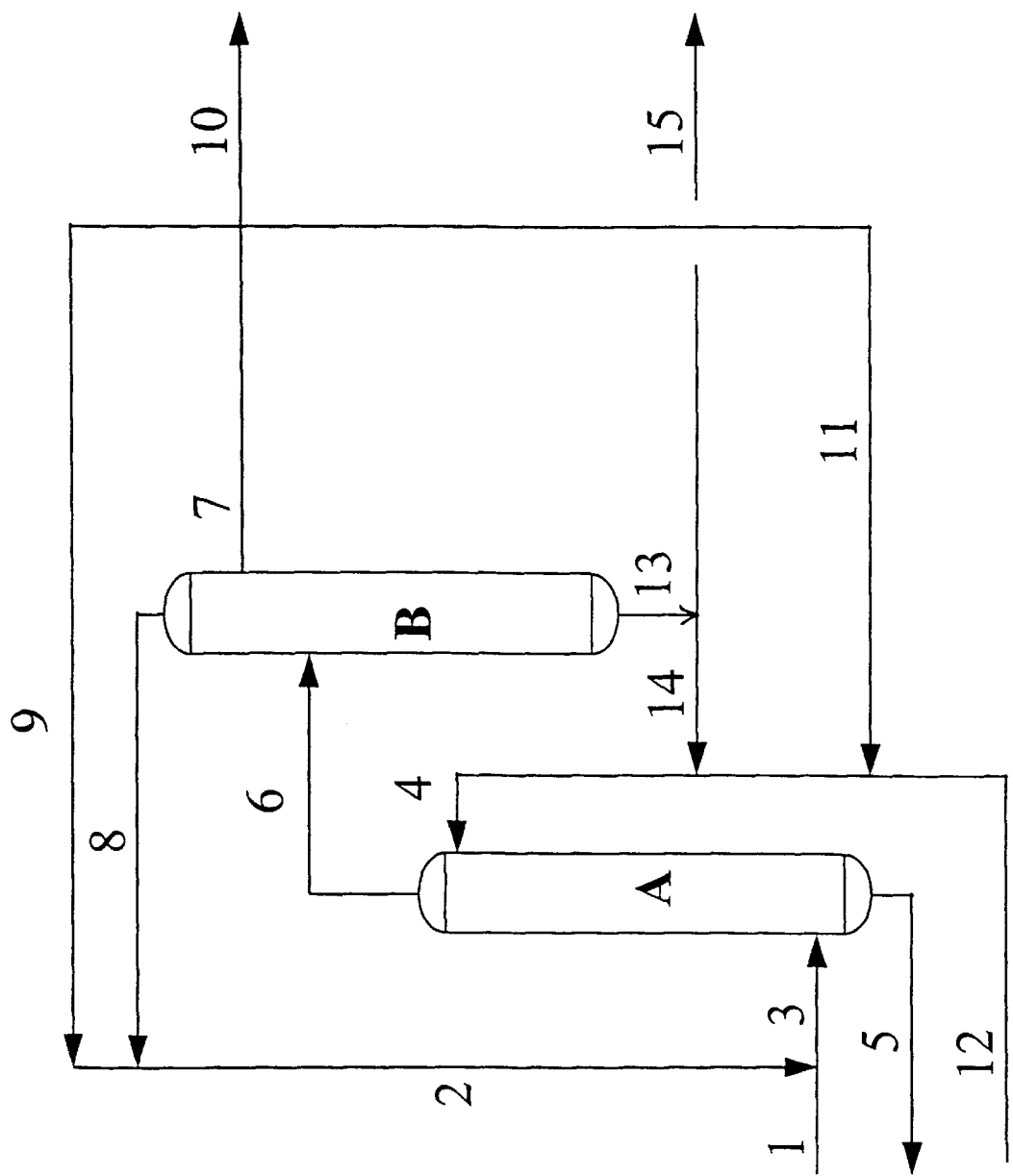

The invention shall be illustrated making use of FIG. 2. The description of the process and the Figure are not intended to limit the invention in any way, but are merely to illustrate one embodiment of the invention. The following abbreviations are used:

DBA 2-methyl glutaric acid
$C_9$ nonanoic acid

In FIG. 2 a purge stream (1) consisting 2 weight units DBA (2 DBA), 0.9 weight units $C_9$ (0.9 $C_9$) and 500 ppm Rh is mixed with 3.1 weight units $C_9$ and 0.7 weight units $H_2O$ (stream (2)). This organic starting mixture (3) is fed to the bottom of extraction column (A). To the top of this column the aqueous solvent consisting of 0.6 $H_2O$, 1 DBA and 0.4 $C_9$ and 0.1 wt % HI is fed (stream 4). At the bottom an aqueous extract (stream 5) is obtained consisting of 725 ppm rhodium (quantitatively removed from purge), 1 DBA, 0.4 $C_9$ and 0.6 $H_2O$ (weight units). This mixture may be reused in the carbonylation reaction. At the top an organic raffinate (stream 6) is obtained consisting of 0.7 $H_2O$, 4 $C_9$ and 2 DBA (stream 6). Stream (6) is distilled in distillation column (B). Three product streams are obtained, namely 4 weight units $C_9$ (stream 7), 0.7 weight units $H_2O$ (stream 8) and 2 weight units DBA (stream 13). 3.1 weight units of the 4 weight units $C_9$ obtained in (B) is mixed with the purge stream via stream (9) and (2). Of the remaining $C_9$ 0.4 $C_9$ is mixed via stream (11) with fresh $H_2O$ stream (12) and used as aqueous solvent (stream 4) in the extraction (A). The remaining 0.5 $C_9$ (stream 10) is free of rhodium. Of the 2 DBA obtained in distillation (B) (stream 13) 1 DBA is used as part of the aqueous solvent (via stream 14) and 1 DBA (free from rhodium) is obtained in stream (15). The above can be summarized as follows:

| in via (1) | in via (12) | out via (5) | out via (10) | out via (15) |
|---|---|---|---|---|
| 0 $H_2O$ | 0.6 $H_2O$ | 0.6 $H_2O$ | 0 $H_2O$ | 0 $H_2O$ |
| 2 DBA | | 1 DBA | 0 DBA | 1 DBA |
| 0.9 $C_9$ | | 0.4 $C_9$ | 0.5 $C_9$ | 0 $C_9$ |
| 500 ppm Rh | | 725 ppm Rh | 0 ppm Rh | 0 ppm Rh |

(*) the numbers are in tons per hour

The invention shall be further illustrated by the following non-limiting examples.

EXAMPLE I

The extraction coefficient $K_{Rh}$ was determined for different compositions of the water, 2-methyl glutaric acid and nonanoic acid ternary system. The results are listed in Table 1. The concentration of rhodium was in the range of 100–400 ppm and the HI/Rh molar ratio was 2. The phases were mixed under 0.1 MPa carbon monoxide pressure.

| water phase H$_2$O (wt %) | 2 MGA (wt %) | C$_9$ (wt %) | organic phase H$_2$O (wt %) | 2 MGA (wt %) | C$_9$ (wt %) | K$_{Rh}$ [water]/ [organic] in ppm |
|---|---|---|---|---|---|---|
| 100 | 0 | 0 | 0 | 0 | 100 | 0.02 |
| 94 | 6 | 0 | 1 | 3 | 96 | 0.07 |
| 81 | 19 | 0 | 1 | 8 | 91 | 0.20 |
| 48 | 46 | 6 | 4 | 18 | 78 | 1.43 |
| 28 | 55 | 17 | 11 | 33 | 56 | 5.00 |

2 MGA = 2-methyl glutaric acid
C$_9$ = nonanoic acid

Resulting K$_{Rh}$ listed in Table 1 illustrate that the extraction efficiency is positively influenced when C$_6$-dicarboxylic acid like 2-methyl glutaric acid is present during extraction.

What is claimed is:

1. Process to separate rhodium from an organic starting mixture comprising an organic solvent, C$_6$-dicarboxylic acids and iodide compounds, wherein rhodium is separated by extracting the organic starting mixture with an aqueous solvent containing C$_6$-dicarboxylic acids and an iodide compound resulting in an organic raffinate poor in rhodium and an aqueous extract rich in rhodium.

2. Process according to claim 1, wherein the ratio of C$_6$-dicarboxylic acid concentration in the aqueous solvent to the C$_6$-dicarboxylic acids concentration in the organic starting mixture is preferably between 1:1 and 5:1.

3. Process according to claim 2, wherein the ratio of C$_6$-dicarboxylic acid concentration in the organic starting mixture to the C$_6$-dicarboxylic acid concentration in the aqueous solvent is about equal to the equilibrium ratio which exists for the C$_6$-dicarboxylic acids over the two phases.

4. Process according to claim 1, wherein the organic solvent is a C$_5$–C$_{13}$ mono-carboxylic acid.

5. Process according to claim 4, wherein the aqueous solvent also contains C5–C13 monocarboxylic acids which correspond to those in organic solvent.

6. Process according to claim 5, wherein the ratio of C$_5$–C$_{13}$ mono-carboxylic acid concentration present in the organic starting mixture to the C$_5$–C$_{13}$ mono-carboxylic acid concentration in the aqueous solvent is between 5:1 and 20:1.

7. Process according to claim 6, wherein the ratio of C$_5$–C$_{13}$ mono-carboxylic acid concentration in the organic starting mixture to the C$_5$–C$_{13}$ mono-carboxylic acid concentration in the aqueous solvent is about equal to the equilibrium ratio which exists for the C$_5$–C$_{13}$ mono-carboxylic acids over the two phases.

8. Process according to claim 1, wherein the iodide compound content in the aqueous solvent is between 0.01 and 10 wt %.

9. Process according to claim 8, wherein the iodide compound is HI.

10. Process according to claim 1, wherein the extraction is performed in the presence of carbon monoxide.

* * * * *